United States Patent [19]
Plyley et al.

[11] Patent Number: 5,678,748
[45] Date of Patent: Oct. 21, 1997

[54] SURGICAL STAPLER WITH IMPROVED SAFETY MECHANISM

[75] Inventors: Alan K. Plyley, Goleta; Claude Vidal, Santa Barbara; Russell J. Redmond, Goleta, all of Calif.

[73] Assignee: VIR Engineering, Santa Barbara, Calif.

[21] Appl. No.: 449,106

[22] Filed: May 24, 1995

[51] Int. Cl.$^6$ ................................................ A61B 17/072
[52] U.S. Cl. .................................... 227/175.4; 227/19
[58] Field of Search ........................... 227/175.1, 175.2, 227/175.3, 175.4, 176.1, 182.1

[56] References Cited

U.S. PATENT DOCUMENTS

| | | | |
|---|---|---|---|
| 5,071,052 | 12/1991 | Rodak et al. | 227/175.2 |
| 5,413,267 | 5/1995 | Solyntjes et al. | 227/175.4 |
| 5,445,304 | 8/1995 | Plyley et al. | 227/180.1 |
| 5,465,894 | 11/1995 | Clark et al. | 227/175.1 |

FOREIGN PATENT DOCUMENTS

| | | |
|---|---|---|
| 579038 | 1/1994 | European Pat. Off. |
| WO 83/02247 | 7/1983 | WIPO |

*Primary Examiner*—Joseph J. Hail, III
*Assistant Examiner*—Jay A. Stelacone
*Attorney, Agent, or Firm*—James E. Brunton

[57] ABSTRACT

A surgical stapler for use by a surgeon to place one or more rows of surgical staples in organs or tissue. The stapler is of a character having a supporting frame, a replaceable staple cartridge, an anvil, a mechanism for approximating the cartridge relative to the anvil, and a mechanism for firing the device so as to crimp the staples against the anvil. The device, while at all times permitting approximation of the cartridge relative to the anvil, provides a novel safety mechanism that clearly indicates to the surgeon that the staples have been fired from the staple cartridge and simultaneously disables the device until it is manually reset.

20 Claims, 7 Drawing Sheets

SURGICAL STAPLER WITH IMPROVED SAFETY MECHANISM

BACKGROUND OF THE INVENTION

1. Field of the Invention

The present invention relates generally to surgical stapling devices. More particularly, the invention concerns a novel surgical stapler that embodies a safety mechanism that clearly indicates to the surgeon that the staples have been fired from the staple cartridge and simultaneously disables the device until it is manually reset.

2. Discussion of the Invention

Surgical staplers are frequently used in surgical procedures for suturing body tissue as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. The staples are generally made of metal, although they can be made from polymers, copolymers and similar materials. During the typical suturing process, push bars within the cartridge are controllably advanced by the actuator mechanism in a manner to urge the staples out of the cartridge, through the tissue and forceably against the anvil.

Possibly the most frequently used type of surgical stapler is the linear stapler, which is a device that enables the surgeon to place one to several (typically 2 to 4) rows of surgical staples in body tissue or organs. By way of example, a typical procedure is a pneumectomy, that is a removal of a portion of a patient's lungs. The linear stapler can be used several times during this procedure, including for the occlusion of the pulmonary artery prior to its resection. For this later use, the surgeon clamps the jaws of the stapler across the artery first, then forms the staples and, prior to reopening the stapler jaws, cuts the artery, using the edge of the staple jaws as a guide.

Some prior art linear staplers of conventional design typically embody a single movable lever which, when initially actuated, causes the stapling cartridge to move into proximity with the anvil against which the staples are intended to be formed. The approximated position is such that the tissue is compressed between the cartridge and the anvil to a thickness small enough to ensure proper staple formation. When the lever is squeezed a second time, the staples are fired, that is the staples are urged toward the anvil thereby penetrating the tissues to be stapled and causing the staples to be formed into a "B"-shaped configuration which ensures tissues coaptation and hemostasis. After the staples are formed, the surgeon can, if he desires, cut the tissue using the edge of the staple jaws as a guide and then reopen the instrument. As the instrument opens, the stapled tissues are freed and the instrument automatically returns to its original starting configuration. On such prior linear staple is sold by 3M Health Care of St. Paul, Minn. under the name and style "Precise PI-55".

The environment in the operating room during a surgical procedure can be, at times, complex and confusing, even for experienced surgeons. For example, during the surgical procedure, the surgeon can easily become distracted and forget whether or not the staples have been fired. In prior art surgical staplers, the surgeon can determine that the instrument has been approximated by merely observing the instrument. However, nothing in the appearance of some the prior art instruments indicates that the staples have been fired. Other prior art instruments, such as the "Precise PI-55" offer a visual indicator, but this indicator is located next to the tissues, i.e. in an area where visibility can be mediocre, and can also be overlooked by a distracted surgeon. This deficiency can create a potentially serious situation since frequently, prior to reopening the instrument, the surgeon cuts the stapled tissues. Should the surgeon erroneously conclude that he has fired the staples when, in fact, he has only approximated the cartridge to the anvil and, therefore, proceed to cut unstapled tissues, a hemorrhage could occur when the surgeon reopens the instrument. This situation is further aggravated by the fact that, as a general rule, the prior art staplers provide so much mechanical advantage to the user that the force needed to be applied on the lever to form the staples is often no greater than the force required to approximate the cartridge to the anvil. Accordingly, not only do the prior art devices fail to provide any compelling visual indication of staple firing, they also fail to provide any tactile feedback that the instrument has, in fact, been fired.

The thrust of the present invention is to provide a simple and easily implemented solution to the problem identified in the preceding paragraphs. More particularly, it is a primary object of the invention to provide an improved lever actuated surgical stapler that includes a safety mechanism that clearly and positively indicates to the surgeon at any time during the surgical procedure whether the staples have, or have not, been fired. As will be better understood from the description that follows, not only does the safety mechanism provide a clear indication that the staples have been fired, it also functions to effectively disable the device until it is manually reset by the surgeon. However, unless and until the staples have actually been fired, the device can be used in normal fashion to clamp and reclamp the tissue as many times as may be required. Stated another way, the novel safety mechanism of the invention comes into play when and only when it is needed. Should the surgeon decide, after clamping the tissues, that they should be repositioned, the instrument can be easily opened as many times as necessary without in any way jeopardizing the effectiveness of the safety mechanism. This is true because actuating of the safety mechanism occurs only as a consequence of actually firing the staples from the staple cartridge.

SUMMARY OF THE INVENTION

It is an object of the present invention to provide a surgical stapler of the character having a supporting frame, a replaceable staple cartridge, an anvil, means for approximating the cartridge relative to the anvil, and means for firing the device so as to crimp the staples against the anvil in a manner to enable the surgeon to substantially simultaneously place one or more rows of surgical staples in organs or tissues. The device, while at all times permitting approximation of the cartridge relative to the anvil, provides novel safety means for positively indicating to the surgeon that the staples have, in fact, been fired from the staple cartridge. In this way, unlike the prior art lever type devices, the device of the present invention can safely be used without fear of cutting the clamped tissues prior to having fired the staples to ensure proper tissue coaptation.

It is another object of the invention to provide a surgical Stapler of the aforementioned character which includes a novel safety mechanism that provides a clear, visual indication to the surgeon that the staples have been fired from the staple cartridge.

Another object of the invention is to provide, in one embodiment of the invention, a surgical stapler of the type described in the preceding paragraph in which the safety mechanism disables the device after staple firing has occurred.

Another object of the invention is to provide a surgical stapler of the character described in which the safety feature of the invention can be easily and inexpensively implemented into the prior art device linear stapler by the addition of only two basic component parts, namely a latching pawl and a biasing spring.

Another object of the invention is to provide a surgical stapler that, following staple firing, can be easily manually reset so that the device can be used to reclamp the tissue at a location proximate the stapled closure to permit ease of cauterization or suturing should fluid oozing be detected.

Another object of the invention is to provide a surgical stapler of the class described which is highly versatile, easy to use, and is of simple construction.

DESCRIPTION OF THE INVENTION

Referring to the drawings and particularly to FIGS. 1 through 4, one form of the apparatus of the invention for simultaneously emplacing a plurality of surgical staples into tissues and organs is there illustrated and generally designated by the numeral 14. The apparatus comprises an elongated supporting frame 16 having a handle portion 18 and a longitudinally spaced apart forward portion 20. Formed on supporting frame 16 proximate forward portion 20 is an anvil assembly 22. In a manner presently to be described, a staple cartridge 24 containing a plurality of surgical staplers therewithin is controllably movable toward and away from the anvil through manipulation of handle portion 18.

Figure 1:
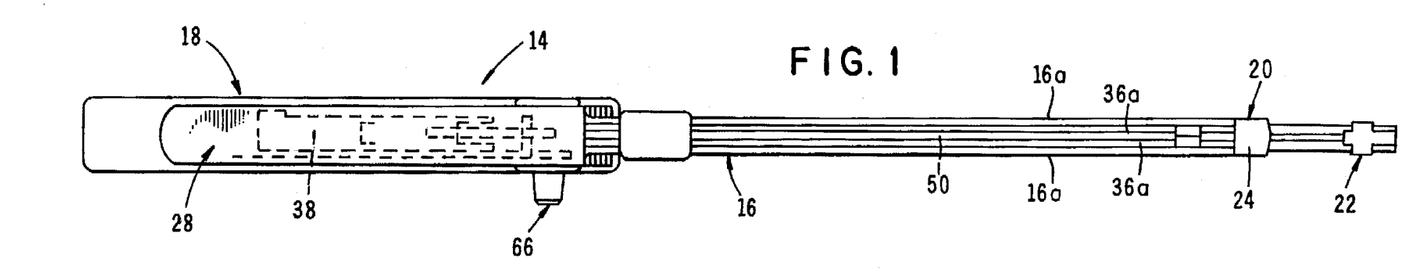
FIG. 1 is a top plan view of one form of the surgical stapler of the present invention.
Figures 2, 15:
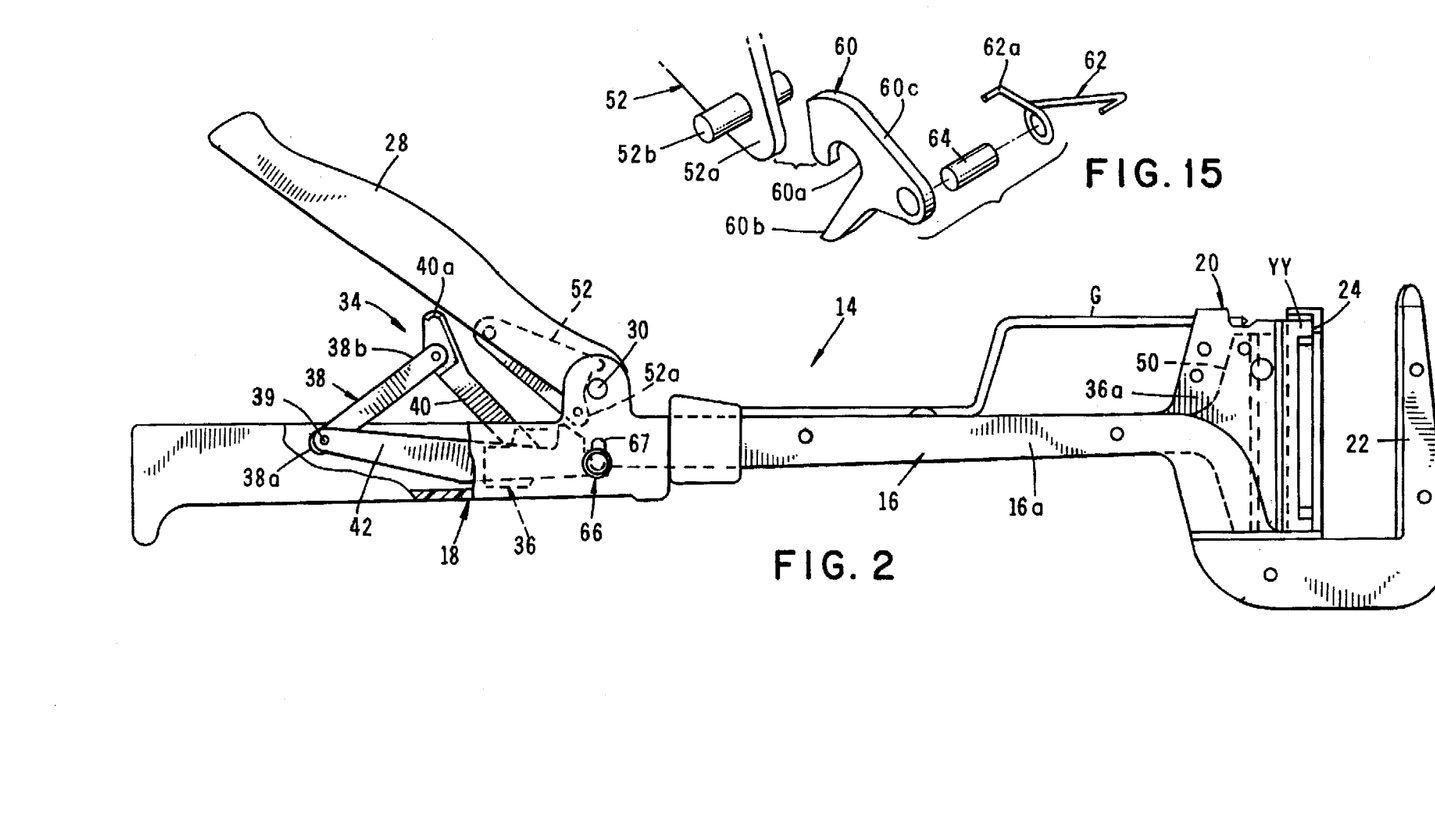
FIG. 2 is a side-elevational view of the surgical stapler partly broken away to show internal construction.
FIG. 15 is a generally perspective, fragmentary, exploded view of the latching pawl mechanism of the apparatus which locks the handle portion in a closed configuration indicating that the staples have been fired.
Figure 3:
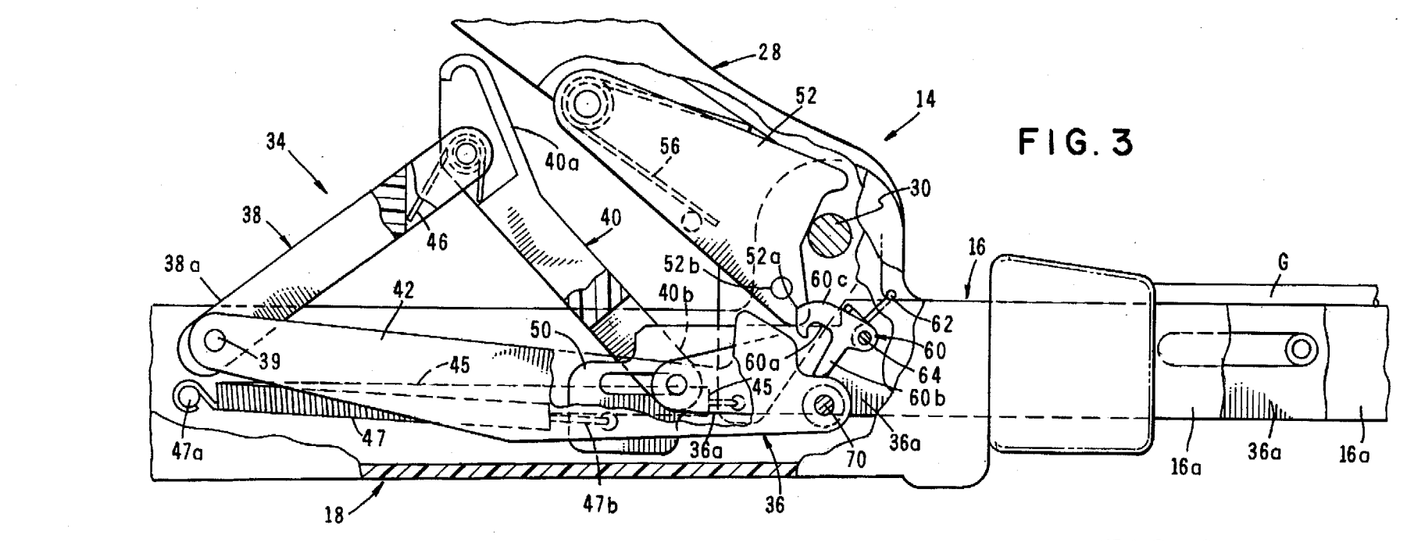
FIG. 3 is an enlarged, fragmentary view of the handle portion of the stapler shown in FIG. 2 partly broken away and partly in cross section to show internal construction.

Forming a part of the handle portion 18 is a lever 28 which is pivotally connected to supporting frame 16 for pivotal movement about a transversely extending pivot pin 30 (FIG. 3). Lever 28 is sequentially movable by a squeezing action applied thereto from a first retracted position shown in FIGS. 2 and 3, to a second closed position shown in FIGS. 5 and 6, to a third retracted position shown in FIGS. 7 and 8 and finally to a fourth closed position shown in FIGS. 9 through 13. In a manner to be described in the paragraphs which follow, movement of the lever between said second, third and fourth positions resulting in approximation of the staple cartridge and the anvil followed by the firing or driving of the staples from cartridge 24 through the tissue clamped between the cartridge and the anvil and into pressural engagement with anvil 22.

To move staple cartridge 24 toward anvil 22 approximation means are provided which here comprise a first operating linkage 34 and an approximation assembly 36. Linkage 34 is carried within the handle portion of supporting frame 16 in the manner shown in FIG. 3 and functions to slide approximation assembly 36 forward within frame 16 upon depressing lever 28 in the manner shown in FIG. 5.

As best seen by referring to FIG. 3, operating linkage 34 comprises first and second pivotally interconnected operating links 38 and 40. The first end 38a of link 38 is pivotally interconnected with frame 16 and with a third link member 42 by a pivot pin 39. The second end 38b of link 38 is pivotally connected to link 40 proximate its first end 40a. The second end 40b of link 40 is operably associated with approximation assembly 36 and moves this assembly forwardly as the linkage is moved into the collapsed overcenter configuration shown in FIGS. 5 and 6. With this construction, when lever 28 is moved from the first position shown in FIGS. 2 and 3 to the second position shown in FIGS. 5 and 6, linkage assembly 34 will be moved by the lever from the extended position shown in FIG. 3 to the collapsed position shown in FIG. 6. As linkage 34 moves into this collapsed, overcenter position, the approximation assembly 36 is urged forwardly to the position shown in FIGS. 5 and 6. A first biasing means shown here as an elongated coil spring 45, (FIG. 3) yieldably resists depression of lever 28. Similarly, a second biasing means, here provided as a torsion spring 46, yieldably resists movement of linkage assembly 34 from the upraised position shown in FIG. 3 to the collapsed or closed position shown in FIGS. 5 and 6. As will be discussed in the paragraphs which follow, spring 46 tends to automatically return linkage 34 to the upraised position when it is moved by a novel release means from the downward, over-center position shown in FIG. 6 toward the open, upstanding position shown in FIG. 3.

Figure 4:
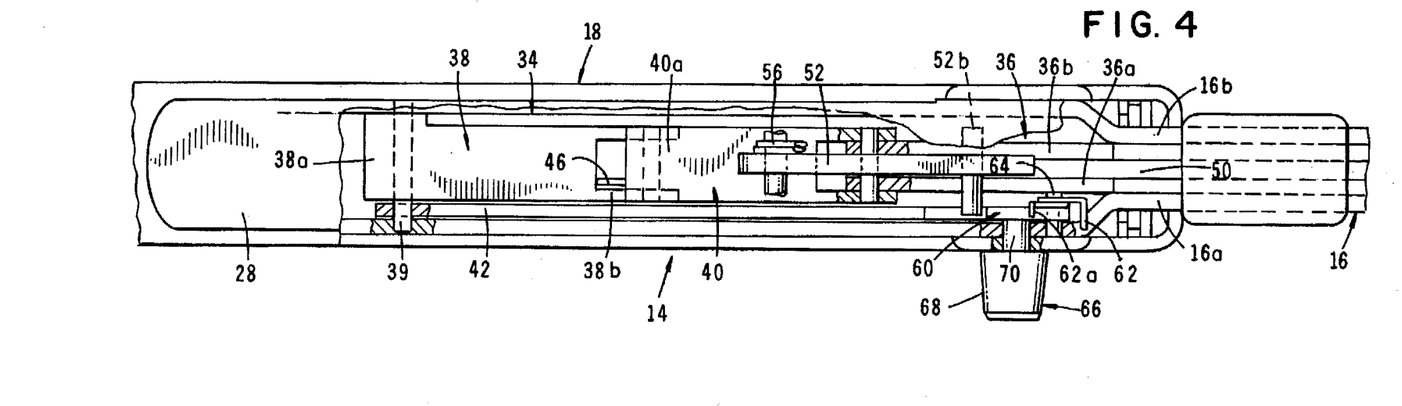
FIG. 4 if a fragmentary, top view of the handle portion of the stapler partly broken away to show internal construction.
Figure 5:
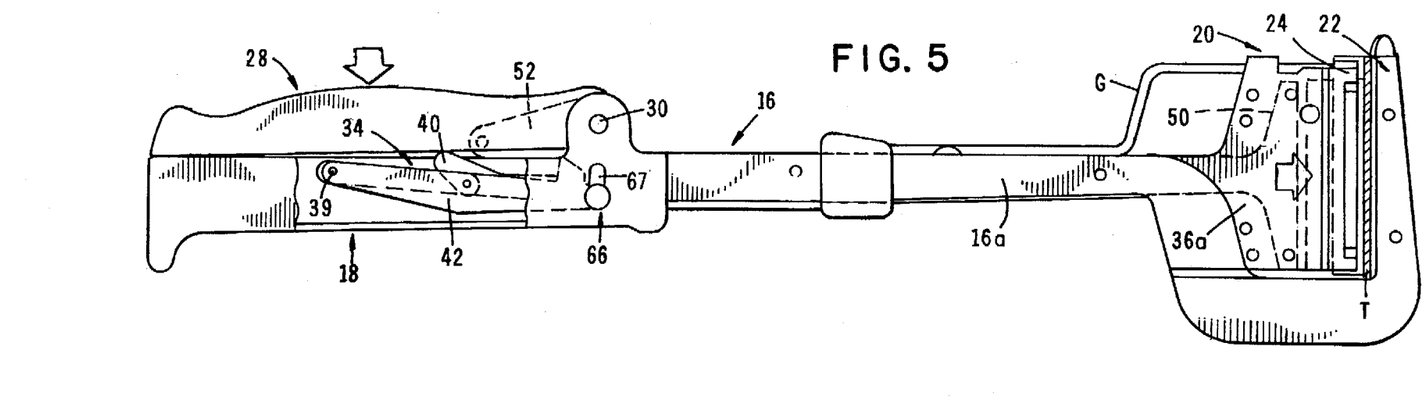
FIG. 5 is a side-elevational view, similar to FIG. 2, but showing the device in an approximated configuration with the staple-holding cartridge moved into close proximity with the anvil of the device.

Turning also to FIG. 4, it can be seen that approximation assembly 36 comprises a pair of spaced-apart, generally "T"

shaped members 36a and 36b which are slidably received within spaced-apart sidewalls 16a and 16b of frame 16. Movement of members 36a and 36b is yieldably resisted by a third biasing means which comprises an elongated coil spring 47 having end 47a connected to the supporting frame and end 46b connected to the approximation members (FIG. 3). Removably connected proximate the forward end of "T" bars 36a and 36b is the previously mentioned staple cartridge 24. With this construction, it is apparent that the forward movement of members 36a and 36b by the initial closing of lever 28 will cause the staple cartridge to move into the approximated position in close proximity with anvil 22 (FIG. 5). The device will remain in this approximated position until it is released by the release means in a manner presently to be described.

Figures 7, 8:
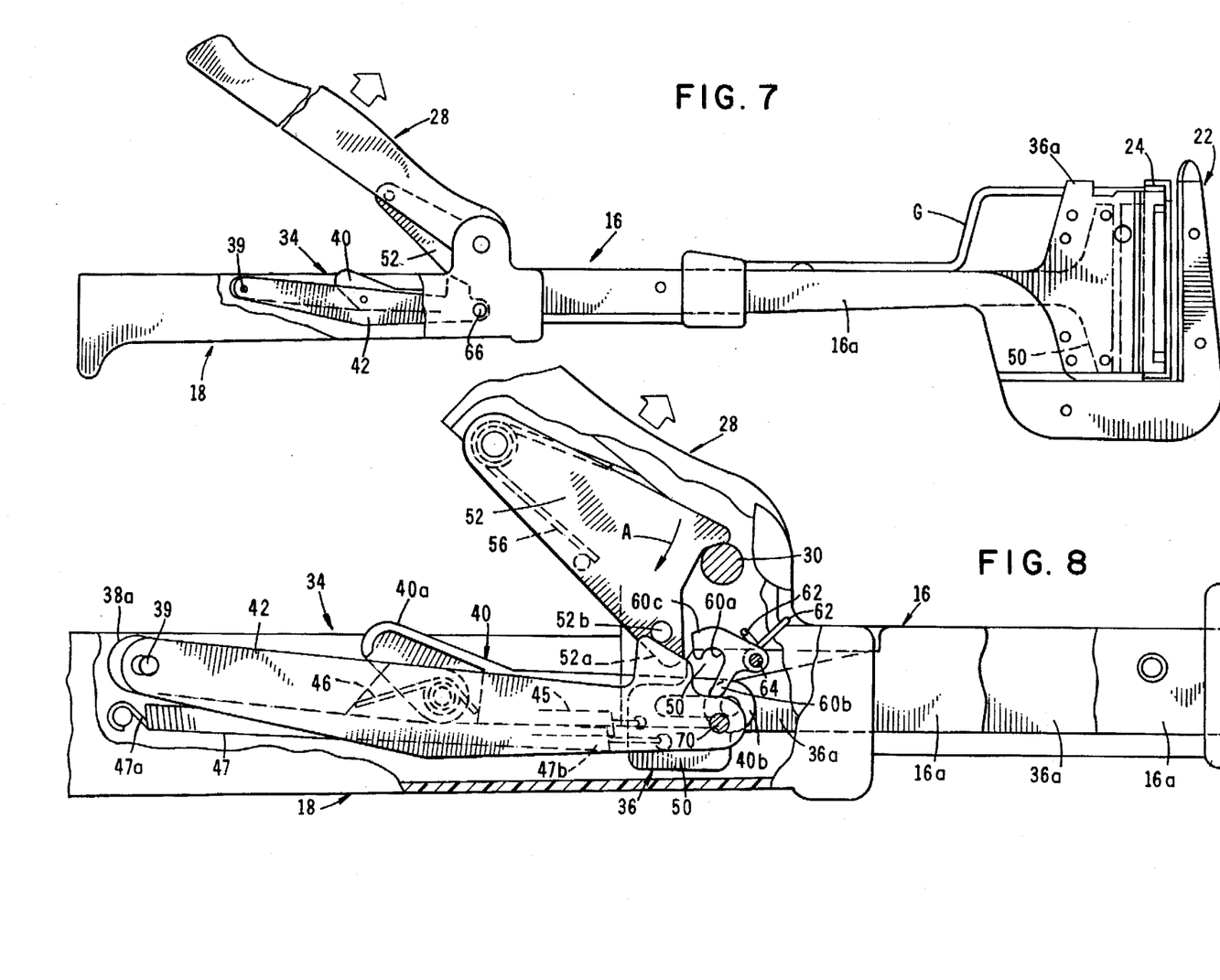
FIG. 7 is a side-elevational view similar to FIG. 5, but showing the device with the actuating lever having returned to an upraised position wherein the apparatus is ready for staple firing.
FIG. 8 is an enlarged, fragmentary view of the handle portion of FIG. 7 partly broken away to show internal construction.

Following the approximation step, the staples can be driven through the tissue "T" and into pressural engagement with the anvil 22 by the operating means of the invention. In the form of the invention shown in the drawings, the operating means comprises an operating bar 50 which is also generally "T" shaped in configuration and is slidably movable between approximation members 36a and 36b from a first retracted position shown in FIG. 4 to a second staple fired position shown in FIGS. 9 through 13. The operating means also comprises an operating member 52 which is pivotally connected to lever 28 for pivotal movement between first and second positions. As best seen in FIG. 8, operating member 52 includes an end portion 52a which is movable into engagement with operating bar 50 following movement of lever 28 to its third retracted position shown in FIG. 8.

Figure 6:
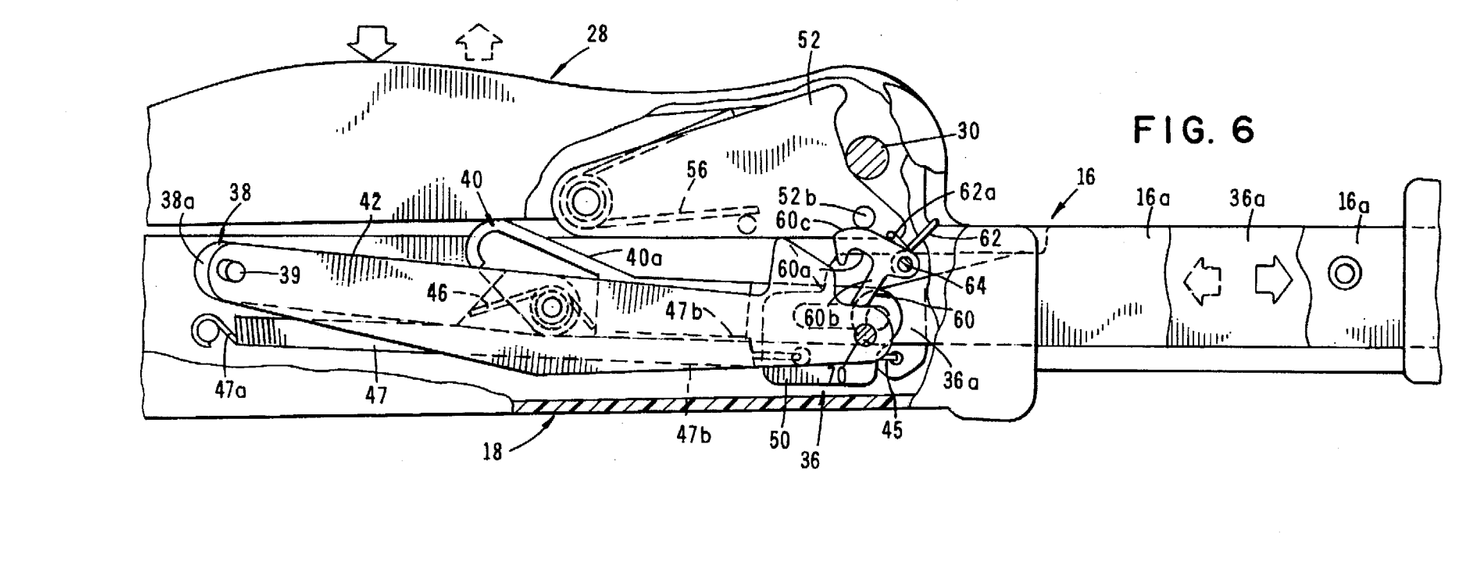
FIG. 6 is an enlarged, fragmentary view of the handle portion of the apparatus as shown in FIG. 5 partly broken away to show internal construction.

As can be observed by also referring to FIGS. 3 and 6, prior to the approximation step, operating member 52 is maintained in its first upraised position by the rearwardly positioned approximation members 36a and 36b. However, upon movement of the approximation members forwardly of the apparatus into the approximated position shown in FIGS. 5, 6, and 8 and upon movement of lever 28 from its second downward position shown in FIG. 6 to its third upward position shown in FIGS. 7 and 8, member 52 will pivot downwardly in the direction of arrow A due to the urging of a fourth biasing means shown here as a torsion spring 56. With member 52 in this downward position, movement of lever 28 into the fourth downward position shown in FIGS. 9 and 10 will cause end 52a of member 52 to engage operating member 50 and cause it to move forwardly from the position shown in FIG. 8 to the forward staple fired position shown in FIG. 10. As member 52 moves forwardly toward staple cartridge 24, it will force the staples from the cartridge through the tissue to be coapted and into pressural engagement with anvil 22. In the prior art staplers, spring 45 would then tend to urge lever 28 into its normal upraised position. Visual observation of the device after firing would, therefore, require that the surgeon both remember to and be able to observe whether carriage pushers YY (FIG. 2) have disappeared from the field of view created by hole XX, which would indicate that the cartridge has been fired, or are still visible, which would indicate that the cartridge has not yet been fired. While this is better than no feedback at all, it is not ideally suited for the busy environment of the operating room nor to the lack of visibility associated with many procedures.

Figure 11:
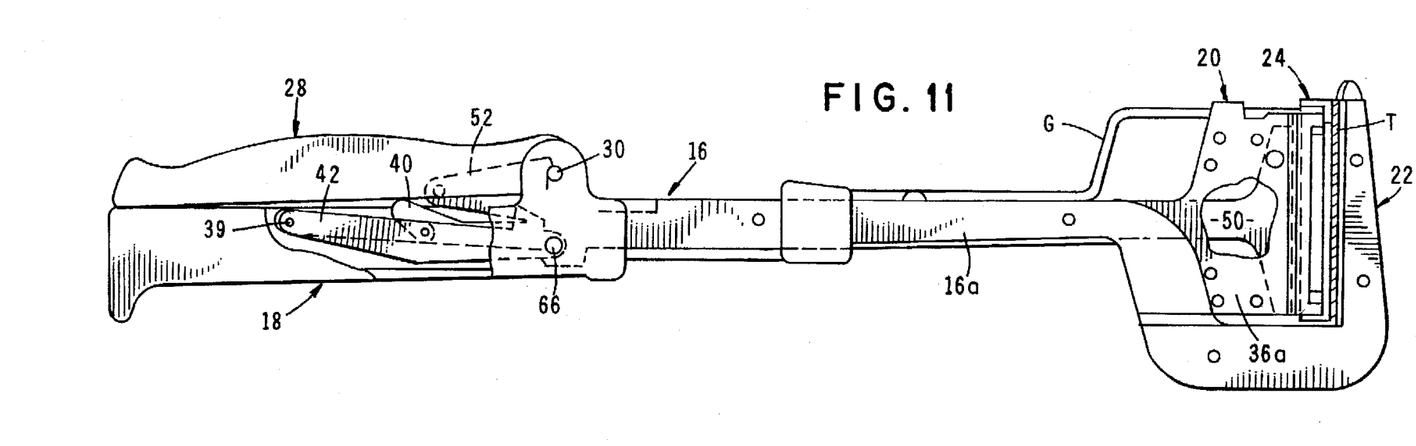
FIG. 11 is a side-elevational view similar to FIG. 9, showing the apparatus as it appears in a static, locked configuration following the staple firing step.
Figure 13:
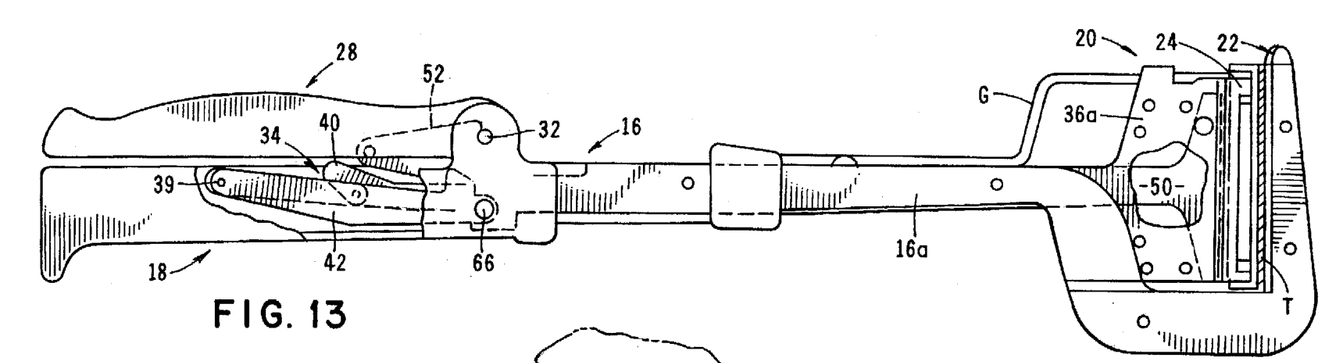
FIG. 13 is a side-elevational view similar to FIG. 11, showing the apparatus in a static safety, locked position prior to operation of the release mechanism.

Forming an important aspect of the present invention is the provision of safety means for releasably securing operating member 52 in its second or downward position while at the same time securing lever 28 in the fourth, downward, or fired position, shown in FIGS. 11 and 13. As best seen by referring to FIGS. 3, 4 and 15, the safety means is here provided in the form of a latching pawl 60 which is pivotally connected to the supporting frame for latching engagement with a transversely extending latching pin 52b provided on operating member 52 (FIG. 15). Also forming a part of the safety means of the invention is a fifth biasing means shown here as torsion spring 62 which functions to continuously bias latching element 60 toward its closed, latched position. Spring 62 encircles a pivot rod 64 about which latching element 60 pivots and includes an end portion 62a which engages the top surface of the latching element 60 in a manner to urge it into a downward latched configuration. As best seen in FIG. 15, latch element 60 also includes a hooklike central portion 60a and a downwardly extending leg portion 60b, the purpose of which will presently be described.

Figure 12:
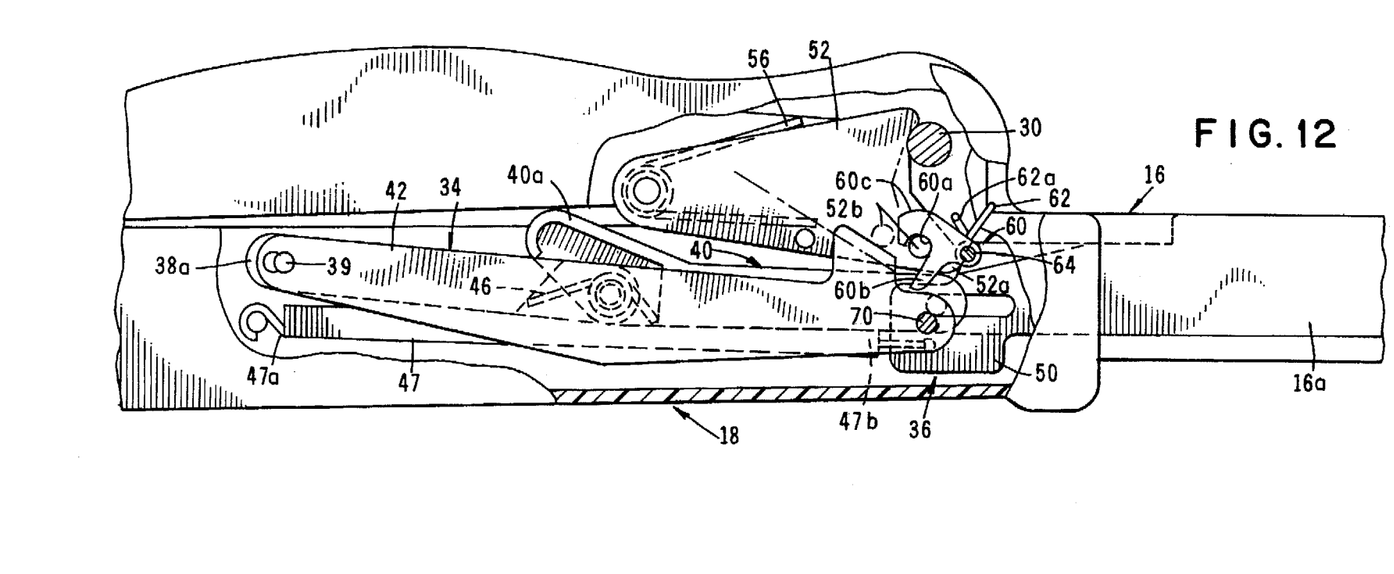
FIG. 12 is an enlarged, fragmentary view of the handle portion of FIG. 11 partly broken away to show internal construction.

Forming another important aspect of the apparatus of the present invention is the provision of release means for releasing operating member 52 and lever 28 from the closed or fired position shown in FIG. 11 and 12. This release means here comprises a manually operated release pin assembly 66 which is movable within a slot 67 formed in the handle portion of the apparatus from a first downward position to a second upward release position. The release pin assembly 66 here includes a knob portion 68 which is interconnected with a shaft portion 70 that extends through and is guided by slot 67. The inboard end of shaft 70 is interconnected with linkage assembly 34 so that an upward movement exerted on knob 68 will move the linkage assembly from the downward, overcenter position shown in FIG. 14 toward the upward, starting position shown in FIG. 3. As knob 68 is moved upwardly, the linkage assembly will rapidly snap into the upward starting position as a result of the action of torsion spring 46.

Figure 14:
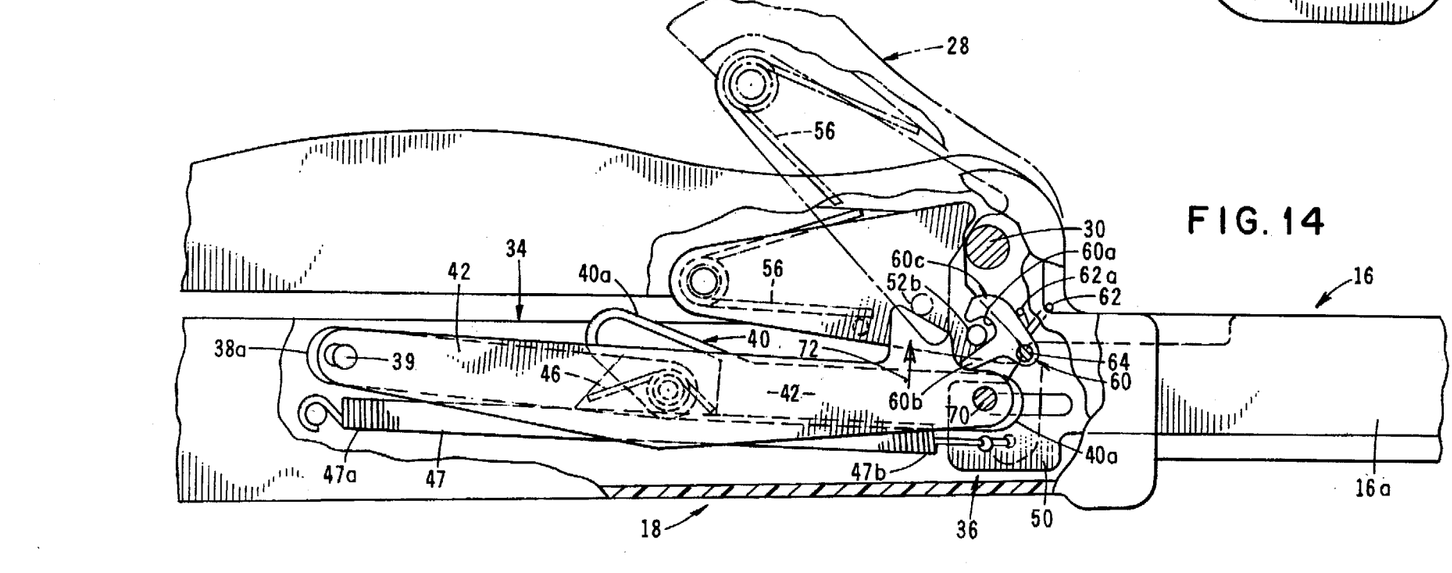
FIG. 14 is an enlarged, fragmentary view of the handle portion of the apparatus of FIG. 13, showing in phantom lines the release of the safety mechanism permitting the handle to return to the staring configuration.

Referring to FIGS. 12 and 14, it is also important to note that as the release means is moved into the upward, release position, linkage member 42 will engage leg 60b of latching member 60 to pivot the member about pin 64 in a clockwise direction as shown in FIG. 14. This clockwise pivotal movement of the latching element causes the hook-like portion 60a of the latching element to move clear of transverse locking pin 52b of operating member 52 thereby freeing the operating member so that it can move from the position shown in the solid lines in FIG. 14 to the position shown by the phantom lines of FIG. 14. By comparing FIGS. 3 and 14, it can be seen that operation of the release means causes the apparatus to move from the fired and locked position shown in FIGS. 11 and 12 into the initial starting configuration shown in FIG. 3. In this configuration, operating member 52 has returned to the upward first or striking position and linkage 34 has also returned to the retracted starting position. Due to the urging of their respective biasing means, the actuating members and operating bar of the apparatus have also returned once more to the starting configuration shown in FIG. 3.

In operating the apparatus of the invention, after a full staple cartridge has been loaded and the elongated guide rod G of the device has been moved rearwardly in the manner shown in FIG. 2 so as to clear the space between the cartridge and the anvil, the tissue, which is coapted, can be appropriately positioned between the staple cartridge and the anvil. This done, the guide rod G, which functions to maintain alignment between the staple cartridge and the anvil, is returned to the forward, closed position shown in FIG. 5. Next, lever 28 is moved from the first, or starting, position shown in FIG. 2 to the second closed position shown in FIG. 5. This action causes the approximation means to controllably move the staple cartridge 24, along with the approximation members 36a and 36b and operating bar 50 forwardly of the apparatus so that the staple cartridge is disposed in close proximity with the face of the anvil 22.

After the staple cartridge and its associated operating bar 50 have been moved into close proximity with anvil 22 and in clamping relationship with tissue "T" (FIG. 5), the apparatus is in condition for the firing or staple crimping operation. As previously discussed, this staple-firing step is accomplished by the operating means of the invention which means is carried by the supporting frame and comprises the generally "T" shaped bar 50 which is slidably disposed intermediate approximation members 36a and 36b (FIG. 4).

With the apparatus in the configuration shown in FIGS. 7 and 8, the staple firing step can be accomplished. More particularly, lever 28, which has now returned to the third open position, is squeezed against the fixed portion of the handle causing the lower tip 52a of operating member 52 to urge operating bar 50 slidably forwardly between member 36a and 36b in the manner shown in FIGS. 9 and 10. This forward movement of T-bar 50 will cause the staples contained within the staple cartridge to be driven forward through the tissue and into crimping engagement with the anvil.

Referring once again, to FIGS. 6 and 8, it is to be noted that during the approximation step (FIG. 6), the locking pin 52b provided on operating member 52 (FIG. 15) has traveled over the curved top surface 60c of locking pawl 60. However, upon movement of lever 28 into its third retracted position shown in FIGS. 7 and 8, the locking pin along with the forward portion 52a of the operating member has dropped downwardly below the level of curved surface 60c of the locking pawl 60.

Figure 9:
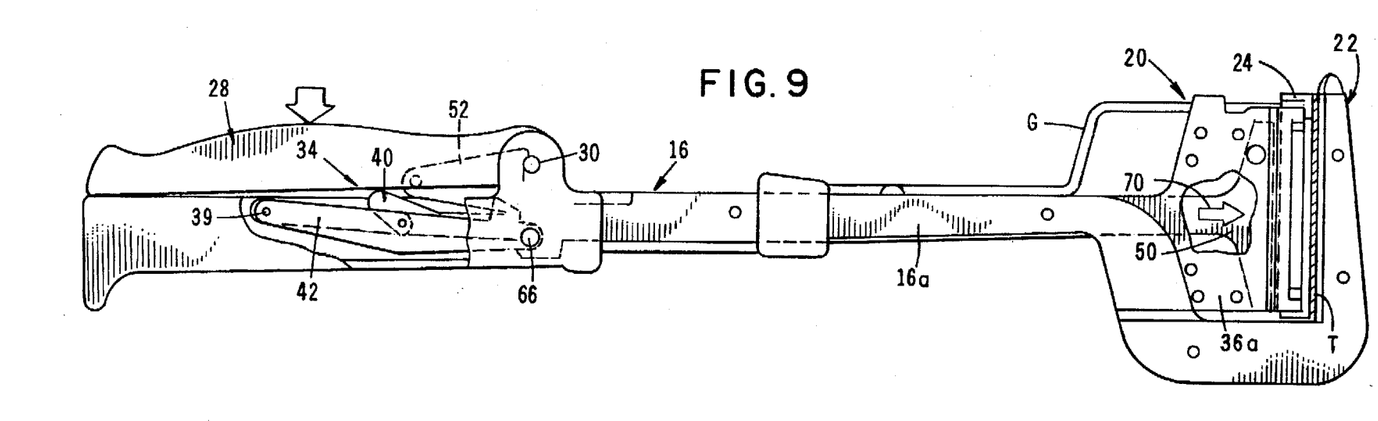
FIG. 9 is a side-elevational view similar to FIG. 7, but showing the apparatus as it appears during the staple firing step.
Figure 10:
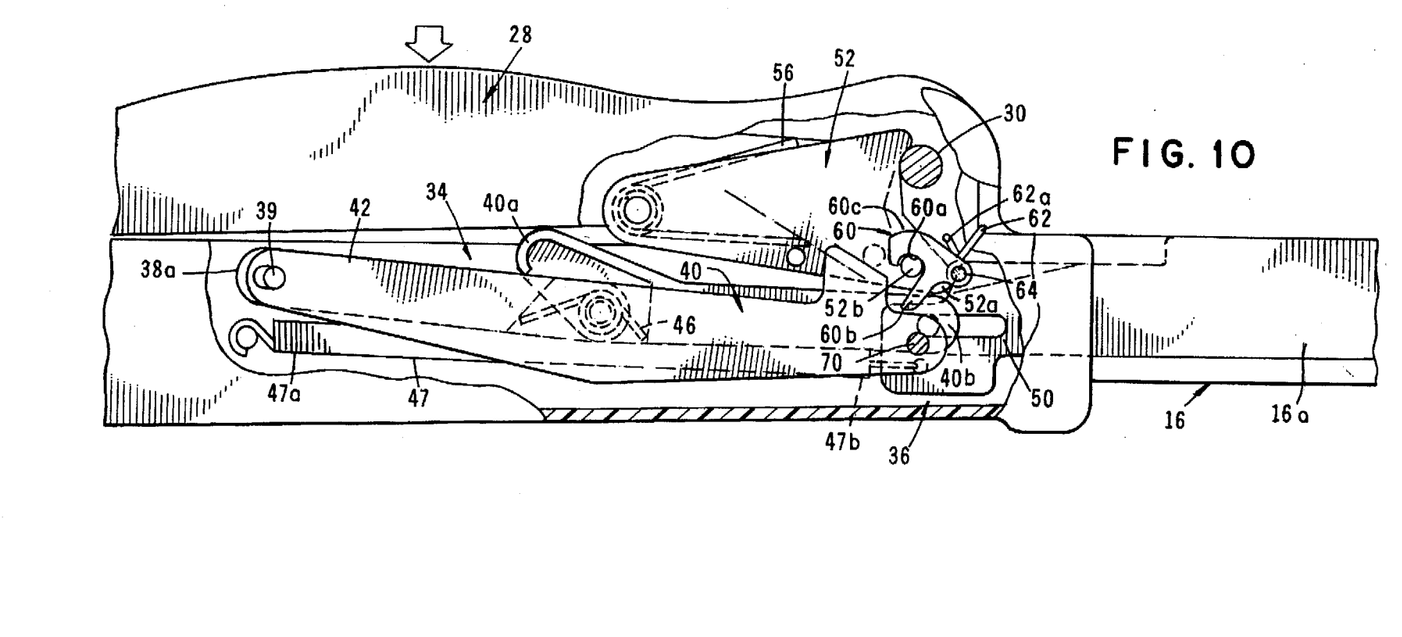
FIG. 10 is an enlarged, fragmentary view of the handle portion of FIG. 9 partly broken away to show internal construction.

Closing of lever 28 by exerting a force in the direction of the arrows in FIGS. 9 and 10, will cause the forward tip of the operating member 52 to engage operating bar 50 urging it forwardly toward the staple cartridge in the direction of the arrow 70 of FIG. 9. As the tip portion 52a of the operating member 52 moves forwardly, transverse locking pin 64 will move under the tip of latching element 60 against the urging of spring 62. Spring 62 will then urge the latching element to move in a counterclockwise direction thereby locking pin 64 within the hooklike opening 60a formed in the latching element.

As indicated in FIGS. 11 and 12 once the latching element has moved into the latching position, operating member 52, as well as lever 28, will be securely locked into the fired, static configuration shown in FIGS. 11 and 12. With the apparatus in this configuration, it is readily apparent to the surgeon that the staples have, in fact, been fired and that the apparatus is temporarily disabled.

To return the apparatus to its starting configuration, knob 68 is urged upwardly in the direction of the arrow 72 in FIG. 14. This causes the counterclockwise movement of latching element 60 in the manner shown in FIG. 14 permitting the operating member 52 to move from the downward locked position into the upward position illustrated by the phantom lines in FIG. 14. At the same time, the linkage assembly 34 will be lifted from its overcenter configuration shown in FIG. 14 to an upward position wherein spring 46 causes it to rapidly retract into the upstanding position shown in FIG. 3. With the operating member, the linkage 34, and lever 28 moved into the upward starting configuration shown in FIG. 3, the device is ready for reuse by the surgeon. It is worthwhile to note that this important additional safety feature does not require any new or additional manipulation on the part of the surgeon familiar with the 3M PI-55 instrument and like devices.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for simultaneously securing a plurality of surgical staples in tissues and organs, including a supporting frame; a staple cartridge containing a plurality of staples movably supported by said frame; an anvil mounted on said supporting frame for engagement by said staples, means for moving said staple cartridge from a retracted position to a clamping position proximate said anvil, said means including a lever pivotally connected to said supporting frame, said lever being movable from a retracted position to a closed position, means for urging said staples into pressural engagement with said anvil, said means for urging said staples into pressural engagement with said anvil comprising an operating member movable between a first position wherein said lever is in said retracted position, to a second position wherein said lever is in said closed position, the improvement comprising safety means for releasably securing said operating member in said second position, thereby locking said lever in said closed position.

2. An apparatus as defined in claim 1 in which said safety means comprises a latching pawl pivotally connected to the supporting frame for latching engagement with said operating member when said operating member is in said second position.

3. An apparatus as defined in claim 1 including biasing means for biasing said lever toward said retracted position.

4. An apparatus as defined in claim 3 including release means carried by said supporting frame for releasing said lever from said closed position, whereby said lever will return to said retracted position.

5. An apparatus for simultaneously emplacing a plurality of surgical staples into tissues and organs comprising:
    (a) an elongated supporting frame having first and second ends;
    (b) an anvil assembly connected to said supporting frame proximate said second end;
    (c) a lever pivotally connected to said supporting frame proximate said second end thereof, said lever being sequentially movable from a first retracted position to a second closed position to a third retracted position and to a fourth closed position.
    (d) approximation means carried by said supporting frame, said approximation means including a first end movable toward said anvil as said lever is moved to said second closed position;
    (e) a staple cartridge removably connected to said first end of said approximation means, said staple cartridge including a plurality of staples;
    (f) operating means carried by said supporting frame for driving said staples from said staple cartridge into pressural engagement with said anvil as said lever is moved toward said fourth closed position; and
    (g) safety means carried by said supporting frame for engagement with said operating means when said lever is moved to said fourth, closed position for releasably locking said lever in said fourth, closed position.

6. An apparatus as defined in claim 5 in which said safety means comprises a latching pawl pivotally connected to said supporting frame, said latching pawl including a latching element for lockably engaging said operating means upon movement of said lever to said fourth closed position to releasably lock said lever in said fourth closed position.

7. An apparatus as defined in claim 6 further including first biasing means carried by said supporting frame for yieldably resisting movement of said lever from said first retracted position toward said second closed position and from said third retracted position toward said fourth closed position.

8. An apparatus as defined in claim 7 further including manual release means carried by said supporting frame for releasing said lever from said fourth closed position.

9. An apparatus as defined in claim 8 in which said approximation means comprises:
 (a) a linkage assembly carried by said supporting frame, said linkage assembly being movable by said lever from a first position to a second position upon movement of said lever toward said second closed position; and
 (b) a pair of approximation members slidably carried by said supporting frame, said approximation members having first end portions adapted to removably receive said stapler cartridge and second end portions operably associated with said linkage assembly whereby movement of said linkage assembly toward said second position will cause movement of said approximation members toward said anvil.

10. An apparatus as defined in claim 9 further including second biasing means for yieldably resisting movement of said linkage assembly toward said second position and third biasing means for yieldably resisting movement of said approximation members toward said anvil.

11. An apparatus for simultaneously emplacing a plurality of surgical staples into tissues and organs comprising:
 (a) an elongated supporting frame having first and second ends;
 (b) an anvil assembly connected to said supporting frame proximate said second end;
 (c) a lever pivotally connected to said supporting frame proximate said second end thereof, said lever being sequentially movable from a first retracted position to a second closed position to a third retracted position and to a fourth closed position;
 (d) approximation means carried by said supporting frame, said approximation means including a first end movable toward said anvil as said lever is moved to said second closed position, said proximation means comprising:
  (i) a linkage assembly carried by said supporting frame, said linkage assembly being movable by said lever from a first position to a second position upon movement of said lever toward said second closed position; and
  (ii) a pair of approximation members slidably carried by said supporting frame, said approximation members having first end and second end portions operably associated with said linkage assembly whereby movement of said linkage assembly toward said second position will cause movement of said approximation members toward said anvil;
 (e) a staple cartridge removably connected to said first end portion of said approximation members, said staple cartridge including a plurality of staples;
 (f) operating means carried by said supporting frame for driving said staples from said staple cartridge into pressural engagement with said anvil as said lever is moved toward said fourth closing position, said operating means comprising an operating member movable between a first and a second position, said operating member having a locking pin;
 (g) safety means carried by said supporting frame for engagement with said operating means when said lever is moved to said fourth, closed position for releasably locking said lever in said fourth, closed position, said safety means comprising a latching pawl pivotally connected to said supporting frame, said latching pawl including a latching element engagable with said locking pin of said operating member, said latching element being adapted to lockably engage said operating means upon movement of said lever to said fourth closed position to releasably lock said lever in said fourth closed position;
 (h) first biasing means carried by said supporting frame for yieldably resisting movement of said lever from said first retracted position toward said second closed position and from said third retracted position toward said fourth closed position.
 (i) second biasing means for yieldably resisting movement of said linkage assembly toward said second position;
 (j) third biasing means for yieldably resisting movement of said approximation members toward said anvil; and
 (k) manual release means carried by said supporting frame for releasing said lever from said fourth closed position.

12. An apparatus as defined in claim 11 further including fourth biasing means for biasing said operating member toward said second position.

13. An apparatus as defined in claim 12 in which said latching pawl is pivotally movable from a first position to a second position upon movement of said lever to said third open position and in which said apparatus further includes fifth biasing means for urging movement of said latching pawl toward said second position.

14. An apparatus as defined in claim 13 in which said manual release means comprises a release pin operably associated with said linkage assembly, said release pin being movable relative to said supporting frame from a first locked position to a second release position causing said linkage assembly to move from said second position to said first position.

15. An apparatus for simultaneously emplacing a plurality of surgical staples into tissues and organs comprising:
 (a) an elongated supporting frame having a handle portion and a longitudinally spaced-apart, forward portion;
 (b) an anvil assembly connected to said supporting frame proximate said forward portion;
 (c) a lever pivotally connected to said supporting frame proximate said handle portion, said lever being sequentially movable from a first retracted position to a second closed position, to a third retracted position and to a fourth closed position;
 (d) a first operating linkage connected to said supporting frame for movement by said lever between first and second positions upon movement of said lever toward said second closed position; and
 (e) a pair of approximation members carried by said frame, said approximation members being slidably movable relative to said frame by said first operating linkage between a first position and a second position upon movement of said lever toward said second closed position;

(f) a staple cartridge containing a plurality of staples removably connected to said approximation members; and (g) operating means carried by said supporting frame for driving said staples from said staple cartridge into pressural engagement with said anvil, said operating means comprising:
 (i) an operating bar slidably movable between said approximation members from a first position to a second position; and
 (ii) an operating member pivotally connected to said lever for engagement with said operating bar to move said operating bar to said second position upon movement of said lever toward said fourth position; and (h) safety means carried by said supporting frame for engaging said operating member to lock said operating member in said second position and to simultaneously lock said lever in said fourth position.

16. An apparatus as defined in claim 15 in which said safety means comprises a latching pawl pivotally connected to said frame, said latching pawl including a latching element for lockably engaging said operating member upon movement of said lever to said fourth closed position.

17. An apparatus as defined in claim 16 further including first biasing means for yieldably resisting movement of said lever to said second and fourth closed positions and second biasing means for yieldably resisting movement of said first operating linkage from said first position toward said second position.

18. An apparatus as defined in claim 17 further including manual release means carried by said supporting frame for releasing said lever from said fourth closed position.

19. An apparatus as defined in claim 18 further including third biasing means for yieldably resisting movement of said approximation members toward said second position and fourth biasing means for biasing said operating member toward said second position.

20. An apparatus as defined in claim 19 in which said latching pawl is pivotally movable from a first position to a second position upon movement of said lever to said third open position and in which said apparatus further includes fifth biasing means for urging said latching pawl toward said second position.

* * * * *